US008684741B2

(12) United States Patent
Kim

(10) Patent No.: US 8,684,741 B2
(45) Date of Patent: Apr. 1, 2014

(54) METHOD AND APPARATUS FOR ANALYZING PATTERN COLORINGS AND EVALUATING PSYCHOLOGICAL STATUS OR DISORDERS IN ART THERAPY

(75) Inventor: Seong-in Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 1508 days.

(21) Appl. No.: 12/289,631

(22) Filed: Oct. 31, 2008

(65) Prior Publication Data

US 2009/0191524 A1  Jul. 30, 2009

(30) Foreign Application Priority Data

Jan. 29, 2008 (KR) .................. 10-2008-0008898
Jan. 29, 2008 (KR) .................. 10-2008-0009002
Jan. 29, 2008 (KR) .................. 10-2008-0009018

(51) Int. Cl.
  *G09B 19/00* (2006.01)
(52) U.S. Cl.
  USPC .................................... 434/236; 434/238
(58) Field of Classification Search
  USPC ........... 434/236–238, 322–365; 600/300–301
  See application file for complete search history.

(56) References Cited

U.S. PATENT DOCUMENTS

2003/0180698 A1*  9/2003  Salerian ................. 434/238

* cited by examiner

*Primary Examiner* — Timothy A Musselman
(74) *Attorney, Agent, or Firm* — Sughrue Mion, PLLC

(57) ABSTRACT

A method and apparatus for analyzing pattern colorings and evaluating various psychological symptoms or disorders in art therapy are disclosed. The method suggests performance-related elements such as completeness, accuracy and degree of concentration as elements, can objectively and quantitatively rate these elements as well as various color-related elements, can detect the changes of these elements in pattern colorings, can estimate the levels and changes of psychological symptoms and disorders and determine whether the symptoms and disorders are serious or not, can acquire various kinds of knowledge in the field of art therapy and establish a knowledge base, and can interpret the pattern colorings based on the analysis and knowledge base. The apparatus consists of units obtaining inputs of characteristics of clients, analyzing and rating the various elements in the pattern colorings, and outputting various kinds of information to the clients, parents, teachers, and art therapists.

18 Claims, 23 Drawing Sheets

(12 of 23 Drawing Sheet(s) Filed in Color)

FIG. 3

METHOD AND APPARATUS FOR ANALYZING PATTERN COLORINGS AND EVALUATING PSYCHOLOGICAL STATUS OR DISORDERS IN ART THERAPY

CROSS-REFERENCE TO RELATED APPLICATIONS

This application claims priority under 35 U.S.C. §119 to Korean Patent Application Nos. 10-2008-8898, 10-2008-9002 and 10-2008-9018, each filed on Jan. 29, 2008, the disclosures of which are incorporated herein by reference in their entireties.

FIELD OF THE DISCLOSURE

The present disclosure relates to art therapy, and more particularly, to a method and apparatus for analyzing pattern colorings and evaluating psychological status or disorders in art therapy, including rating color-related and performance-related elements and using a knowledge base.

BACKGROUND

Coloring given patterns, including the mandala patterns, is known to be an effective art therapy tool in evaluating various kinds of psychological or mental status or disorders.

Art therapists can obtain considerably accurate information on psychological status or disorders from a relatively meager reaction expressed in art. Analysis of pattern colorings provides art therapists with useful information for evaluating clients' psychological status or disorders including, but not limited to, feelings of insecurity, guilt, having nightmares, attention deficit and hyperactivity disorder (ADHD), and trauma.

In art therapy, art therapists observe shapes, symbols, lines, colors, etc. in an art piece. In a piece of work where given patterns are colored, color-related elements are the most important elements. Up to now, there has been no scheme in which a computer system with a knowledge base analyzes and rates color-related elements automatically. In addition, the performance-related elements such as completeness, accuracy and degree of concentration, which are believed to be critical to the effectiveness of evaluating coloring patterns as an art therapy tool, have not been considered. Completeness refers, for example, to the ratio of the area (the number of pixels) painted to the total area. Accuracy refers, for example, to the ratio of the area painted correctly within boundaries to the total area. Degree of concentration is estimated by a function of various formal elements such as the color-related elements (including, but not limited to, the number and list of colors used, the number of clusters, and length of edges), completeness and accuracy.

The levels of a client's psychological status or disorders are closely related to the elements in coloring patterns. However, up to now, there has been no suitable method of rating these elements objectively and numerically. Also, there has been no method of estimating the level of psychological status or disorders based on these rated elements.

Accordingly, there has been no expert system approach which can be used as a very useful approach for art therapy.

SUMMARY

Therefore, an objective of at least one of the disclosed embodiments is to provide a method and apparatus for analyzing pattern colorings in art therapy and evaluating psychological status or disorders, which include rating color-related and performance-related elements and using a knowledge base.

Another objective is to provide a method and apparatus for analyzing pattern colorings in art therapy and evaluating psychological status or disorders, which include suggesting performance-related elements, such as the completeness, the accuracy and the degree of concentration in the work of coloring patterns.

Another objective is to provide a method and apparatus for analyzing pattern colorings in art therapy and evaluating psychological status or disorders, which include automatically providing objective and quantitative information based on an analysis and rating of the color-related elements.

Another objective is to provide a method and apparatus for analyzing pattern colorings in art therapy and evaluating psychological status or disorders, which including automatically providing objective and quantitative information based on an analysis and rating of the performance-related elements such as completeness, accuracy and degree of concentration.

Another objective is to provide a method and apparatus for analyzing pattern colorings in art therapy and evaluating psychological status or disorders, which include estimating the level of a client's psychological status or disorders and determining whether the level of the client's psychological status or disorders is serious or not by providing objective and quantitative ratings of the elements in pattern colorings.

Another objective is to provide a method and apparatus for analyzing pattern colorings in art therapy and evaluating psychological status or disorders, which include detecting changes of pattern colorings and providing corresponding knowledge when a series of the pattern colorings are given.

Another objective is to provide a method and apparatus for analyzing pattern colorings in art therapy and evaluating psychological status or disorders, which can detect changes in psychological status or disorders.

Another objective is to provide a method and apparatus for analyzing pattern colorings in art therapy and evaluating psychological status or disorders, which can establish a knowledge base and utilize it.

Another objective is to provide a method and apparatus for analyzing pattern colorings in art therapy and evaluating psychological symptoms or disorders, which can save art therapists' time and effort used in analyzing general pattern colorings and evaluating psychological status or disorders, by automatically analyzing pattern colorings with a computer in a short period of time.

With a view towards these and other purposes and advantages as embodied and broadly described herein, a method for evaluating psychological status or disorders in accordance with an aspect of a disclosed embodiment includes: obtaining personal characteristics of the client from replies to the questionnaires; receiving pattern colorings from the client; rating color-related elements of the colored patterns; rating the performance-related elements such as the completeness, the accuracy and the degree of concentration of the colored patterns; rating the degree of concentration from the color-related elements, the completeness, and the accuracy; and detecting the changes in the pattern colorings, thereby applying an expert system approach and establishing knowledge relevant to the purposes of the methods for evaluating psychological status or disorders.

With a view towards the above and other purposes and advantages as embodied and broadly described herein, an apparatus for evaluating psychological status or disorders and rating elements includes: a unit for receiving colored patterns of clients; a unit for rating the color-related elements, and the performance-related elements such as the completeness, the accuracy and the degree of concentration of the received colored patterns; a unit for providing the clients with questionnaires, and obtaining the clients' personal characteristics; a knowledge base for storing knowledge relevant to rating elements, evaluating pattern colorings, detecting changes, and art therapy which connects the personal characteristics, the color-related elements, and the performance-related elements such as the completeness, the accuracy, and the degree of concentration; a unit for providing the clients, parents, teachers or art therapists with the information obtained by the apparatus.

The foregoing and other objectives, features, aspects and advantages of the disclosed methods and apparatuses will become more apparent from the following detailed description read in the context of the drawings, which include illustrations of pattern colorings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing discussion will be understood more readily from the following detailed description when considered with the accompanying drawings, wherein

FIG. 3 is an example of questionnaires to obtain personal characteristics of clients;

DETAILED DESCRIPTION

The various disclosed embodiments may be embodied in different forms, and some embodiments are illustrated using pattern colorings and will be described in greater detail in the foregoing detailed description. However, it should be understood that this description should not be construed as limiting the various embodiments set forth herein. Instead, the description is intended to accommodate or include modifications, equivalents and substitutes to the described embodiments as would be appreciated by one skilled in the art. Moreover, the detailed description of functions and configurations which are well known, the inclusion of which may unnecessarily obscure the essential points of the disclosed embodiments, are omitted.

The following detailed description is provided so that this disclosure will be thorough and complete, and will fully convey the scope of the disclosed embodiments to one skilled in art therapy.

Terms such as "first" and "second" may be used to describe various elements, but the elements are not limited to the terms. The terms are only used as a purpose of discriminating one element from another element.

Terms used in the present specification are merely used for describing specific embodiments and are not intended to be limiting. Unless a singular expression clearly denotes a different meaning in context, it includes the meaning of a plural expression. In the present application, it is understood that the terms "include" or "have" intend to indicate the existence of features, numerals, steps, operations, elements and components described in the present specification or the existence of the combination of these, and do not exclude the presence of one or more other features, numerals, steps, operations, elements and components or the presence of the combination of these or additional possibility beforehand.

Hereinafter, specific embodiments will be described in detail with reference to the accompanying pattern colorings.

In the following detailed description, the mandala patterns will be described as an example of patterns. However, this is for describing one embodiment. It is apparent to one skilled in art therapy that the disclosed embodiments are not limited to apply only to mandala patterns and instead can be applied to various patterns.

Figure 1:
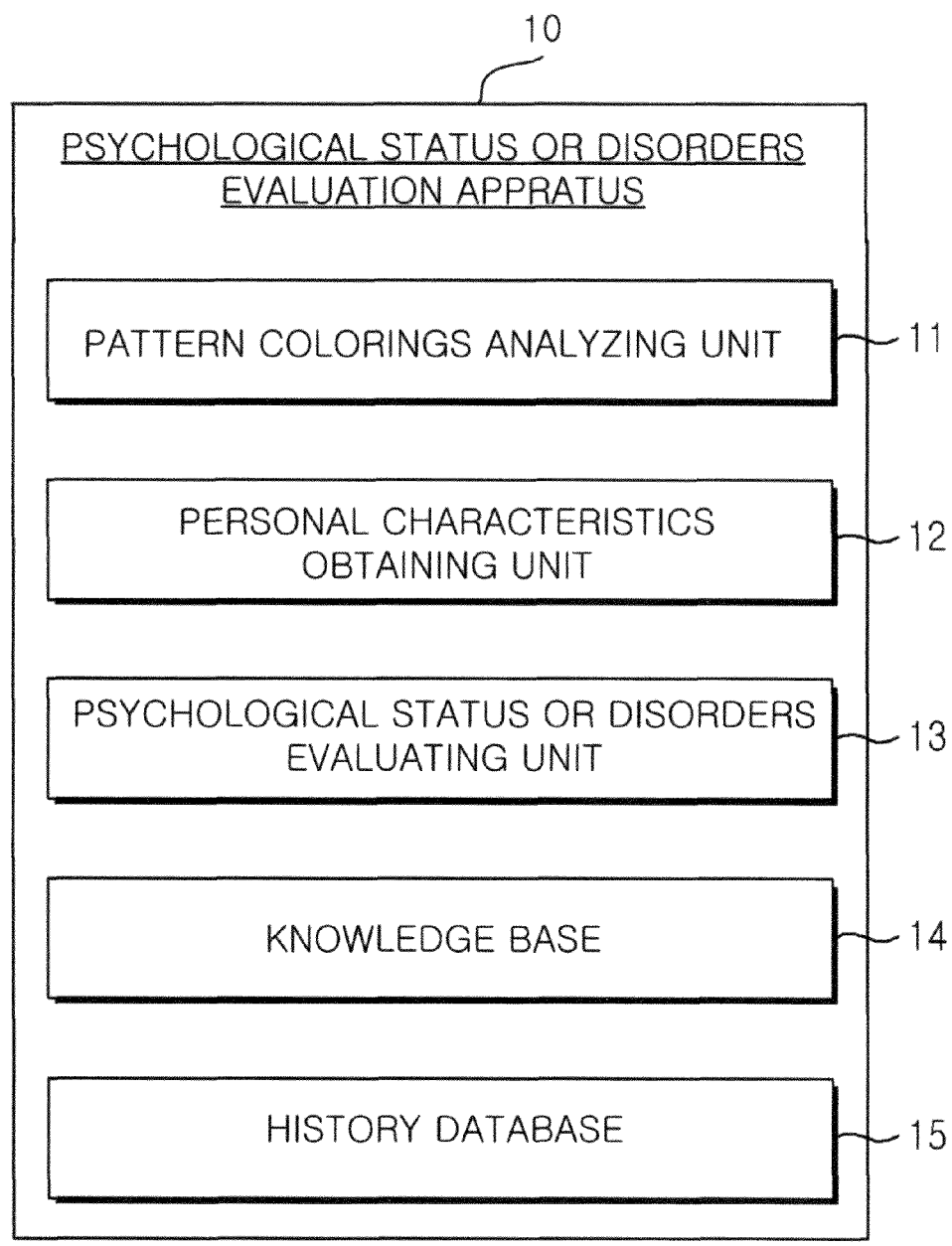
FIG. 1 is a block diagram of an apparatus for evaluating psychological status or disorders according to a disclosed embodiment.
Figure 2:
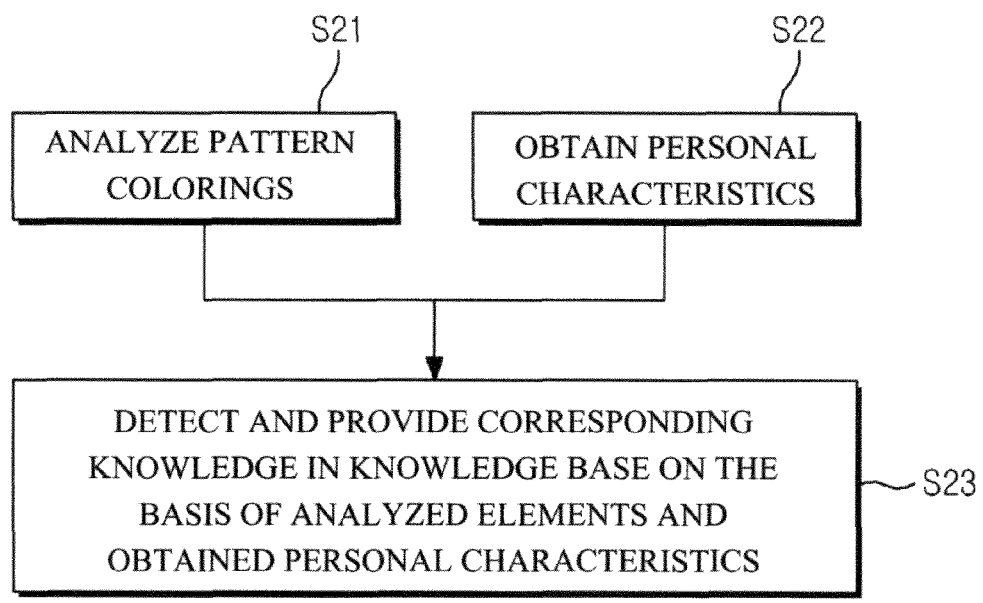
FIG. 2 is a flow chart of a method for evaluating psychological status or disorders according to a disclosed embodiment.
Figure 3:
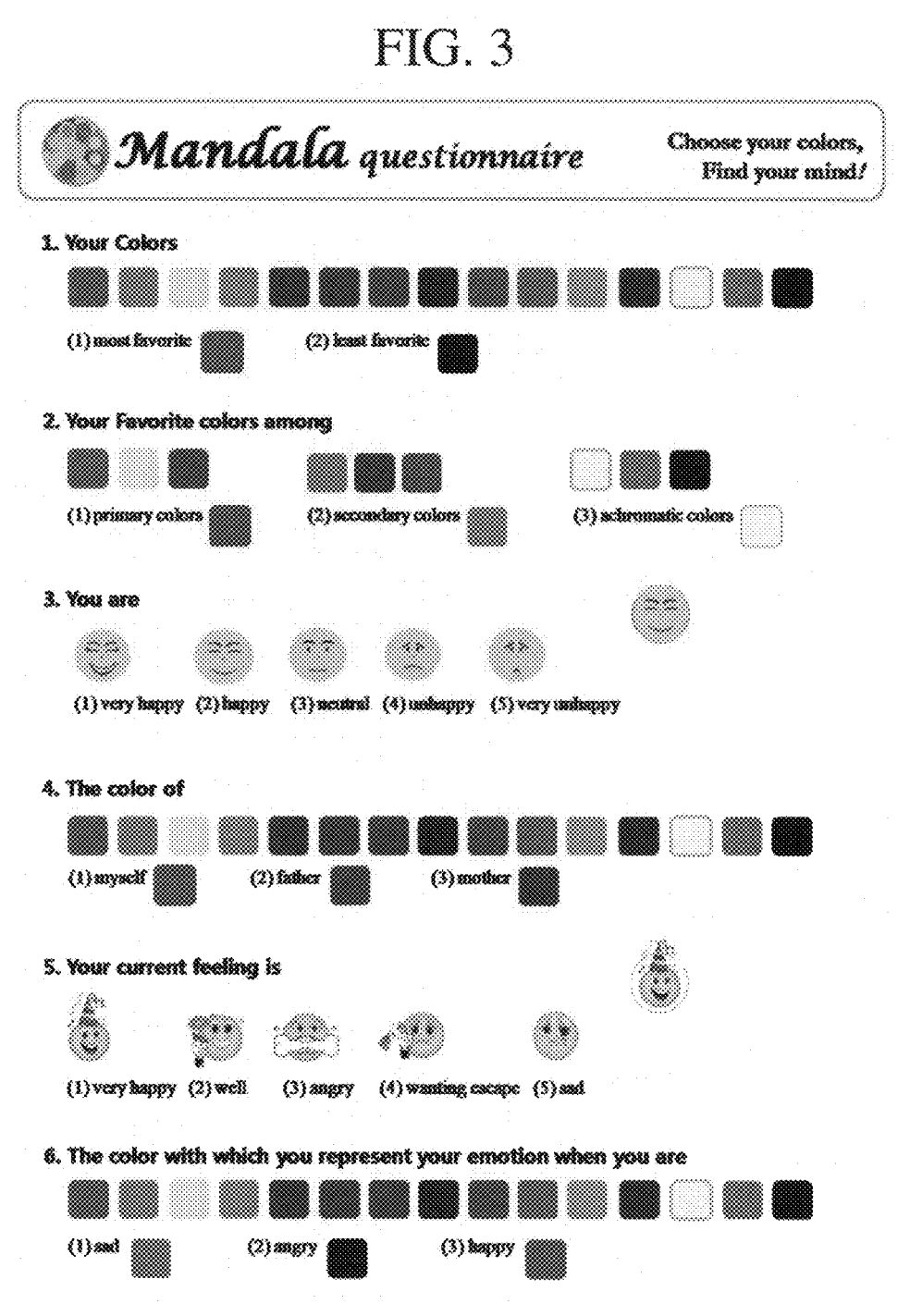

FIG. 1 is a block diagram of an apparatus for evaluating psychological status or disorders according to a disclosed embodiment. FIG. 2 is a flow chart of a method for evaluating psychological status or disorders according to a disclosed embodiment. FIG. 3 is an example of questionnaires used to obtain characteristics of clients.

Referring to FIG. 1, a psychological status or disorders evaluating apparatus 10 according to a disclosed embodiment is illustrated. Herein, the psychological status or disorders evaluating apparatus 10 includes a pattern colorings analyzing unit 11, a personal characteristics obtaining unit 12, a psychological status or disorders evaluating unit 13, a knowledge base 14, and a history database 15. Moreover, the psychological status or disorders evaluating apparatus 10 may further include an input unit (not shown) for receiving a pattern coloring from clients, wherein the input unit may be included in the pattern colorings analyzing unit 11.

The pattern colorings analyzing unit 11 allows clients in art therapy to select a desired pattern among various patterns. Generally, the pattern colorings analyzing unit 11 analyzes patterns colored by clients (for example, children, people for art therapy, etc.) and provides the analysis results of various elements including, but not limited to, the color-related elements, completeness, accuracy, degree of concentration, in quantitative data in step S21. The pattern colorings analyzing unit 11 will be described in detail with reference to FIGS. 4 to 16.

The personal characteristics obtaining unit 12 obtains personal characteristics through some questionnaires in step S22. Referring to FIG. 3, a questionnaire form according to an embodiment is illustrated. The questionnaires are related to aspects including, but not limited to, the client's personal preference of color (see questions 1 and 2), the client's current psychological states (see questions 3 and 5), and the inclination of color (see questions 4 and 6).

Such a questionnaire may be provided to the client for evaluation through a user interface included in the psychological status or disorders evaluation apparatus 10. A display screen provides an interface, such as that illustrated in FIG. 3, to a client for evaluation. Furthermore, the client clicks or drags and drops a color or icon corresponding to each of the questions. Accordingly, the psychological status or disorders evaluation apparatus 10 can obtain information of the personal characteristics of the client. Alternately or in combination, a client for psychological status or disorders may input a numeral, sign, character, or other input corresponding to colors pertinent to each of the questions, the psychological status or disorders evaluation apparatus 10 may obtain information regarding the personal characteristics of the client.

It may be performed in specific order or at the same time that the pattern colorings analyzing unit 11 receives a pattern coloring and analyzes it, and the personal characteristics obtaining unit 12 provides some questionnaires and obtains replies to the questionnaires.

The psychological status or disorders evaluation unit 13 detects knowledge stored in the knowledge base related to the elements such as the color-related elements, completeness, accuracy, degree of concentration, etc., analyzed by the pattern colorings analyzing unit 11 and a personal characteristics information obtained from the personal characteristics obtaining unit 12. Furthermore, the psychological status or disorders evaluating unit 13 puts out knowledge according to the result of the analysis and evaluation of the psychological status or disorders of the client using the output knowledge in step S23. In the evaluation of the psychological status or disorders, knowledge stored in the knowledge base 14 and a past history information (for example, the analysis results of patterns colored by the client) stored in the history database 15 can be used.

The knowledge base 14 stores a variety of data and logic including, but not limited to, knowledge of the selection and arrangement of patterns, knowledge of the colors of a general picture, knowledge of colors expressed in the pattern colorings (for example, mandala patterns or other patterns), knowledge connecting knowledge of the colors and personal characteristics information, and knowledge of psychological changes obtained from the difference between two or more pattern colorings.

A variety of knowledge may be stored and accumulated in the knowledge base 14. Illustrative examples of the variety of knowledge and portions thereof are described below.

In one embodiment, the knowledge is expressed in "IF THEN" format. The form is not strict, but flexible enough for some parts to be changed and even to be omitted depending on the properties of the knowledge. For example, the knowledge may be expressed as follows:

IF [condition-1, or condition-2, or . . . , or condition-n],
THEN [result-1, and/or result-2, . . . , and/or condition-m].
(confidence level of results: references).

An expression includes n conditions and m results. An expression without a condition is possible for universally true facts. Each condition may include several "and" conditions. The content within the double quotation marks is treated as a condition or a result. Confidence level 1 means "occasionally (probability of up to 0.3)", level 2 "may be (probability of up to 0.5)", . . . , and level 5 "certainly (probability of 1.0)."

The following knowledge concerning the relationship between the number of colors used and some psychological disorders illustrates an example of knowledge expressions: "There are reports that child victims of severe sexual abuse and depressed patients tend to use only one or two colors in their drawings. The victims of trauma express their psychological pain, anxiety, fear, sorrow, loneliness, and hopelessness by selecting colors. Children who experienced natural disasters such as earthquakes, hurricanes, and plane crashes tend to use a limited number of colors, not more than two or three, mostly consisting of black, white, and sometimes red."

[Knowledge 1]
IF the number of colors used ≤2,
THEN experience of severe sexual abuse, and/or depression.

[Knowledge 2]
IF the number of colors used ≤3 and colors used=black, or white, or red,
THEN victims of trauma with psychological pain, anxiety, fear, sorrow, loneliness, and hopelessness.

[Knowledge 3]
IF the number of colors used ≤3 and colors used=black, or white, or red,
THEN experience of natural disaster such as earthquakes, hurricanes, or plane crashes.

The following knowledge concerning the relationship between the number of colors used and some psychological disorders illustrates another example of knowledge expressions: "According to Fincher, when red occupies a large area or appears frequently in a mandala, it shows a healthy existence and energy for change to understand inner wisdom in the positive respect, and anger and pain accompanying hurt and destruction in the negative respect."

[Knowledge 4]
IF the main color is red, or the main or subsidiary color is red in 3 mandalas among 4 consecutive mandalas,
THEN healthy existence, and/or energy for change to understand inner wisdom in the positive respect, or anger or pain accompanying hurt and destruction in the negative respect (3: Fincher).

The following knowledge concerning the evaluations of the psychological status or disorders, by connecting the personal characteristics in the answers to the questionnaire with the elements in the mandala, illustrates yet another example of knowledge expressions: "When the personal color representing his or her happiness appears in the mandala, he or she may feel happy."

[Knowledge 5]
IF input-color of happiness=main color,
THEN current emotional status=happy (1).

The following knowledge is yet another example of knowledge expressions concerning changes in pattern colorings:

[Knowledge 6]

IF percentage of warm colors in previous mandala× 1.3≤percentage of warm colors in present mandala, THEN "You are more liberal and active in the expression of your feelings."

A variety of knowledge in art therapy can be stored and accumulated in the knowledge base according to the various embodiments. It is apparent, however, that the embodiments are not limited to the above examples of knowledge. The knowledge base 14 may store knowledge having various contents other than the above-described knowledge.

The history database 15 stores the analysis results of patterns colored by the client, which are compared with each other and can be used in detecting the changes of psychological status or disorders of the client.

Moreover, the psychological status or disorders evaluation apparatus 10 may further include a result providing module. The result providing module may provide pattern colorings analyzing results described below with reference to FIG. 19 and psychological status or disorders evaluating results described below with reference to FIG. 21.

Hereinafter, the pattern colorings analyzing unit 11 will be described in detail with reference to FIGS. 4 to 16.

Figure 4:
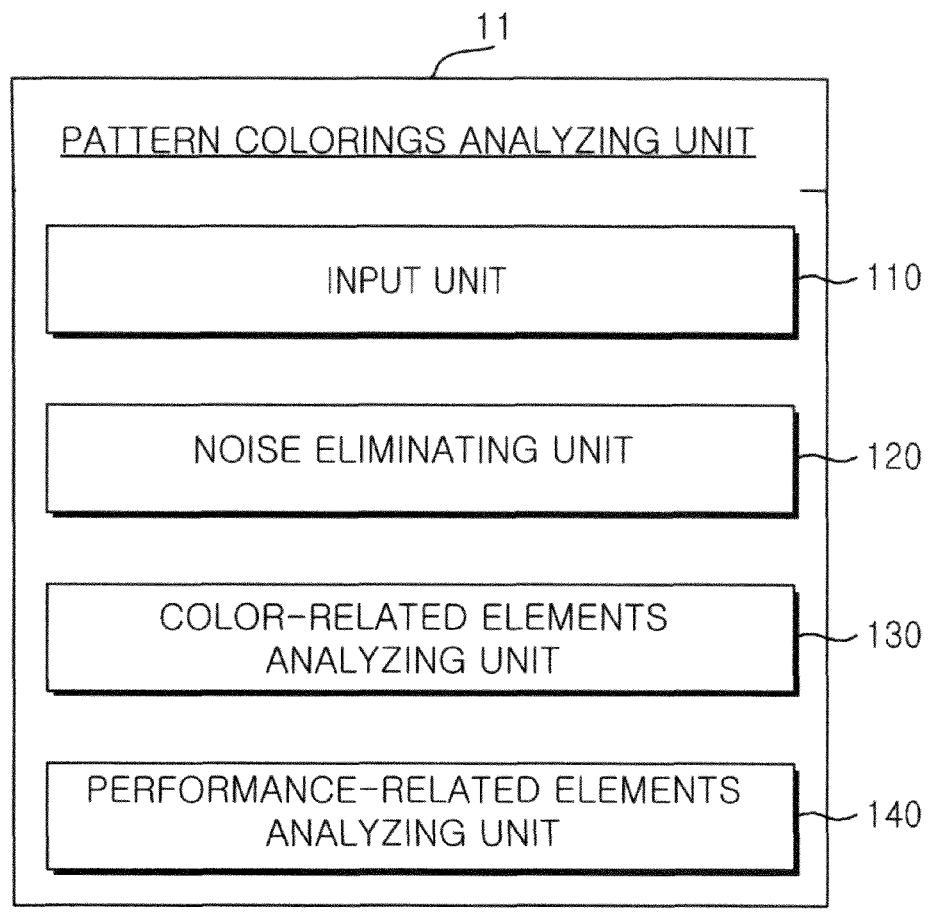
FIG. 4 is a block diagram of the pattern colorings analyzing unit according to a disclosed embodiment.
Figure 5:
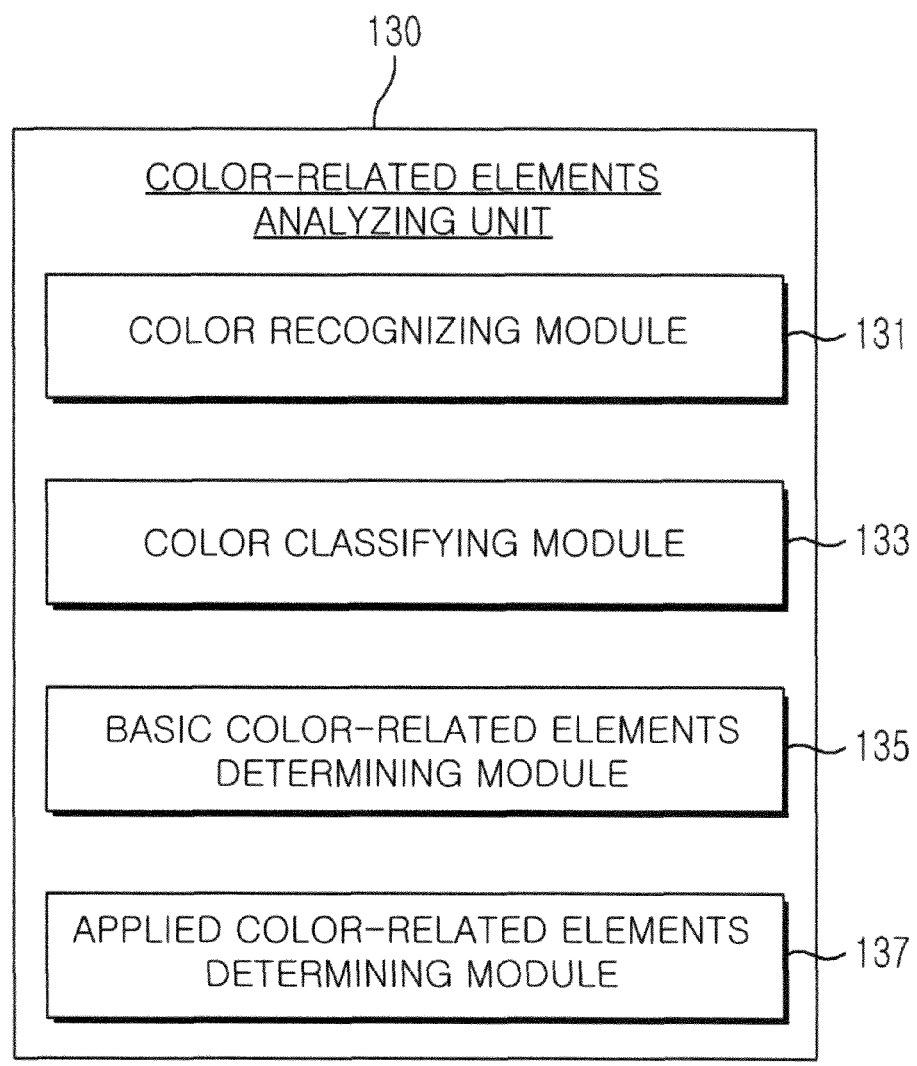
FIG. 5 is a block diagram of a color-related elements analyzing unit included in a pattern colorings analyzing unit.
Figure 6:
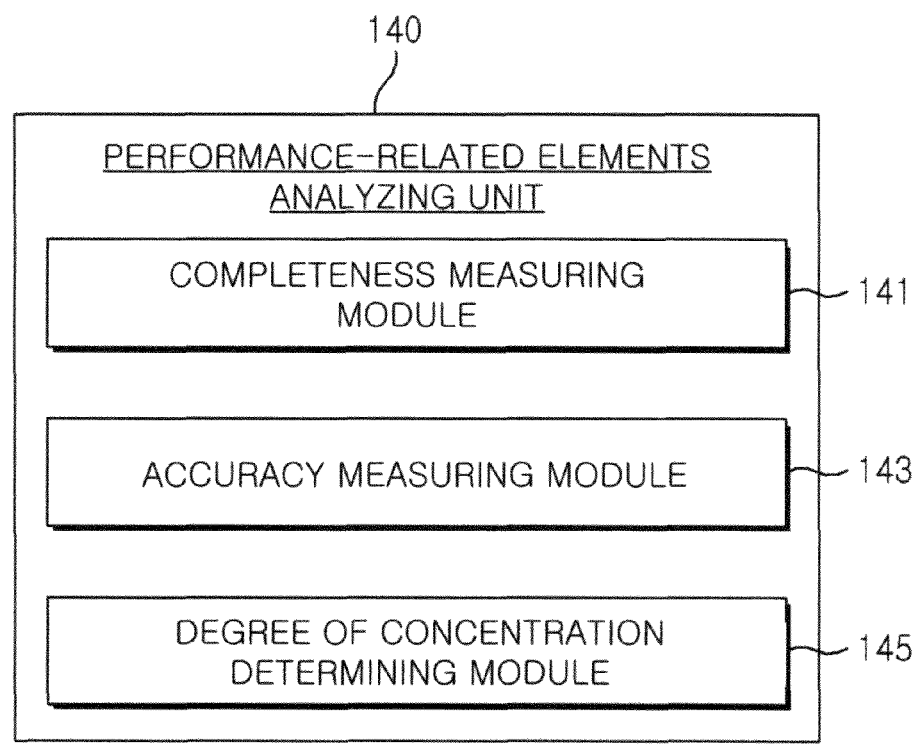
FIG. 6 is a block diagram of a performance-related elements analyzing unit included in a pattern colorings analyzing unit.
Figure 7:
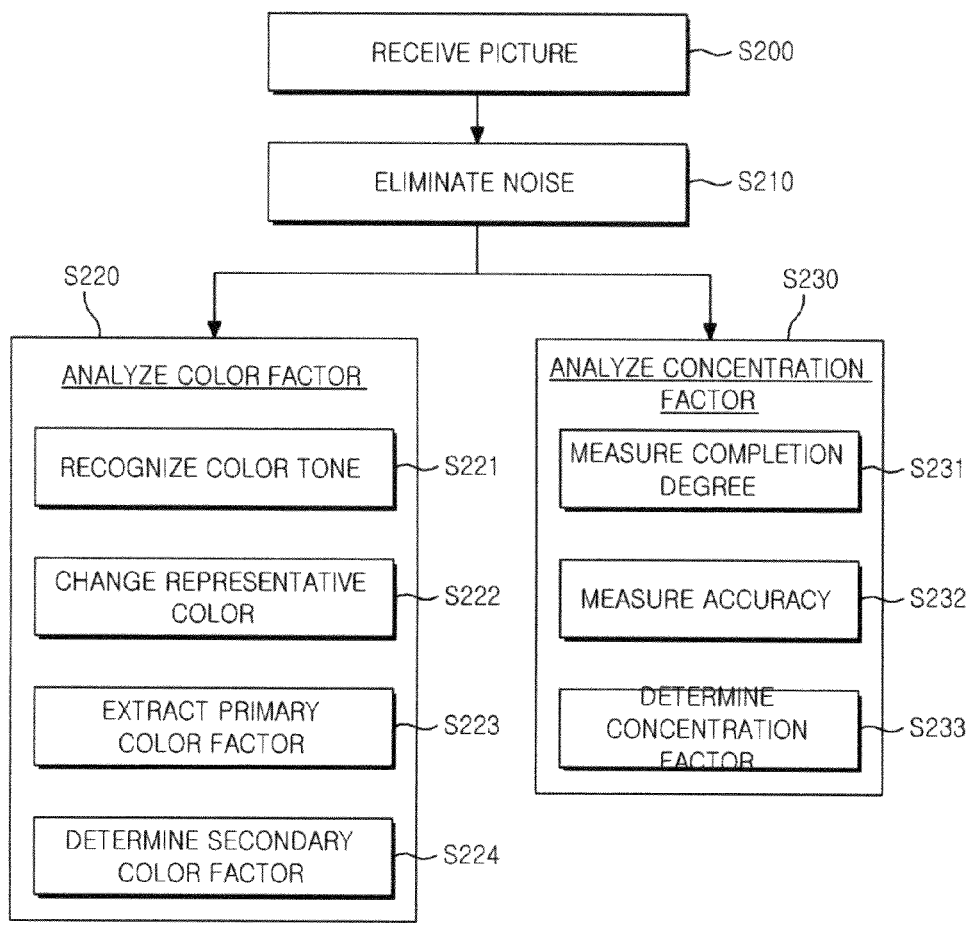
FIG. 7 is a flowchart of a pattern colorings analyzing method according to a disclosed embodiment.
Figure 8:
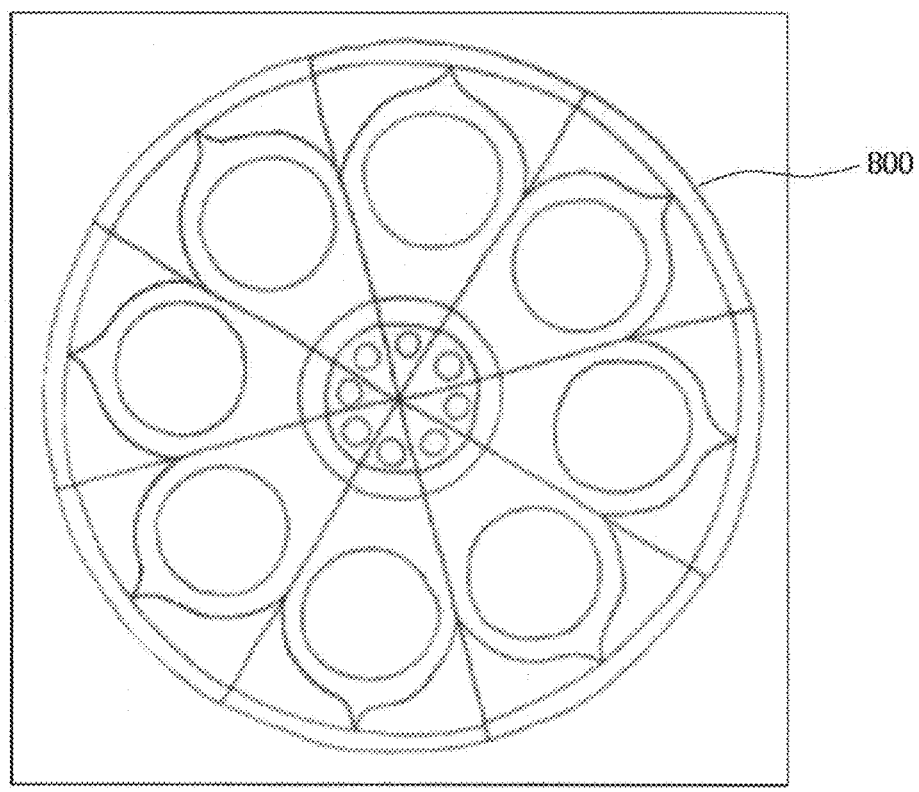
FIG. 8 illustrates an example of patterns according to a disclosed embodiment.
Figure 9:
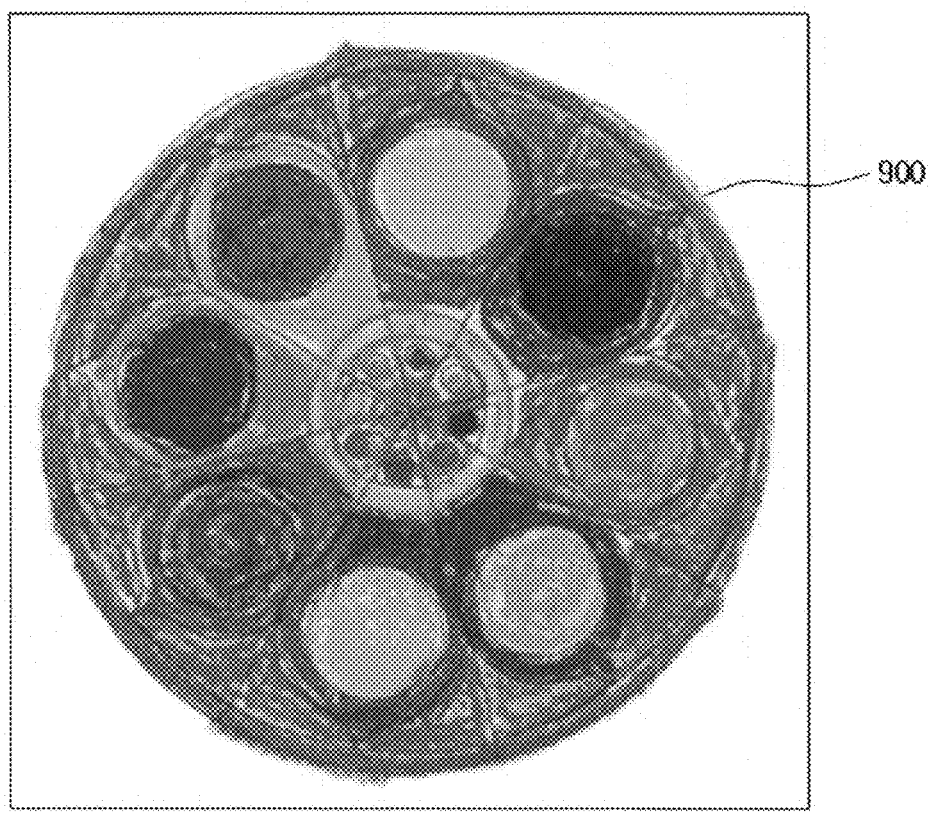
FIG. 9 illustrates a pattern coloring of FIG. 8.
Figure 10:
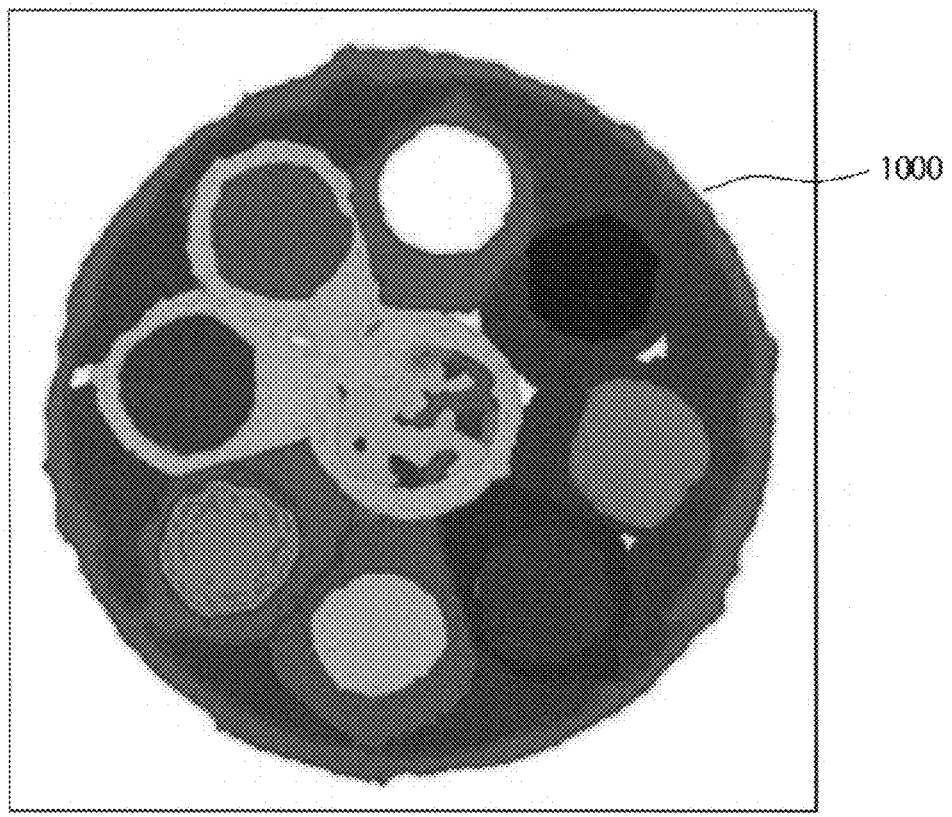
FIG. 10 illustrates a case in which the colors in the pattern coloring of FIG. 9 are classified into one of standard colors.
Figure 11:
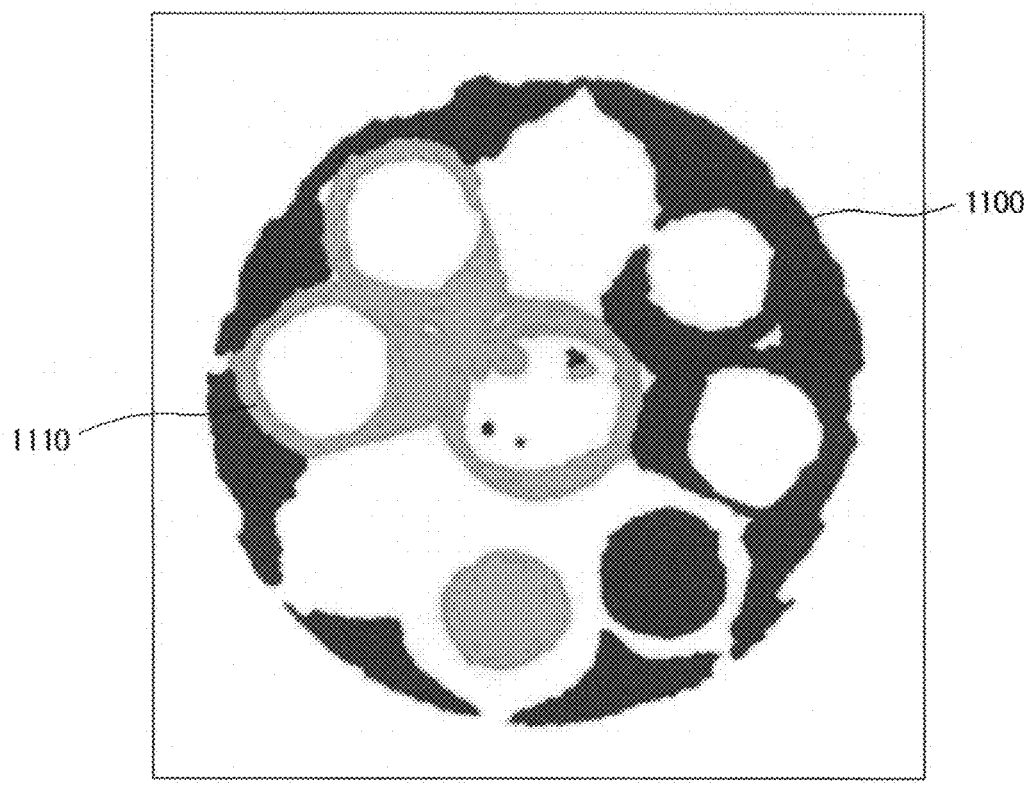
FIG. 11 illustrates classification of colors in pattern coloring of FIG. 10 into main, subsidiary, and complementary colors.
Figure 12:
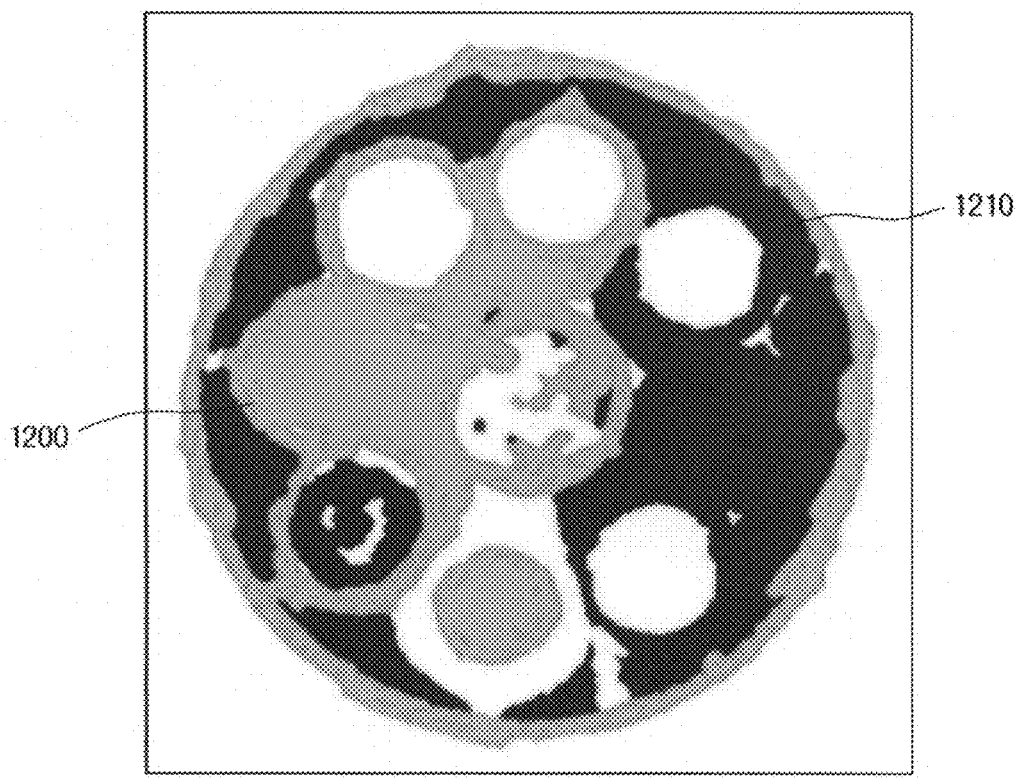
FIG. 12 illustrates classification of colors in pattern coloring of FIG. 10 into primary and secondary colors.
Figure 13:
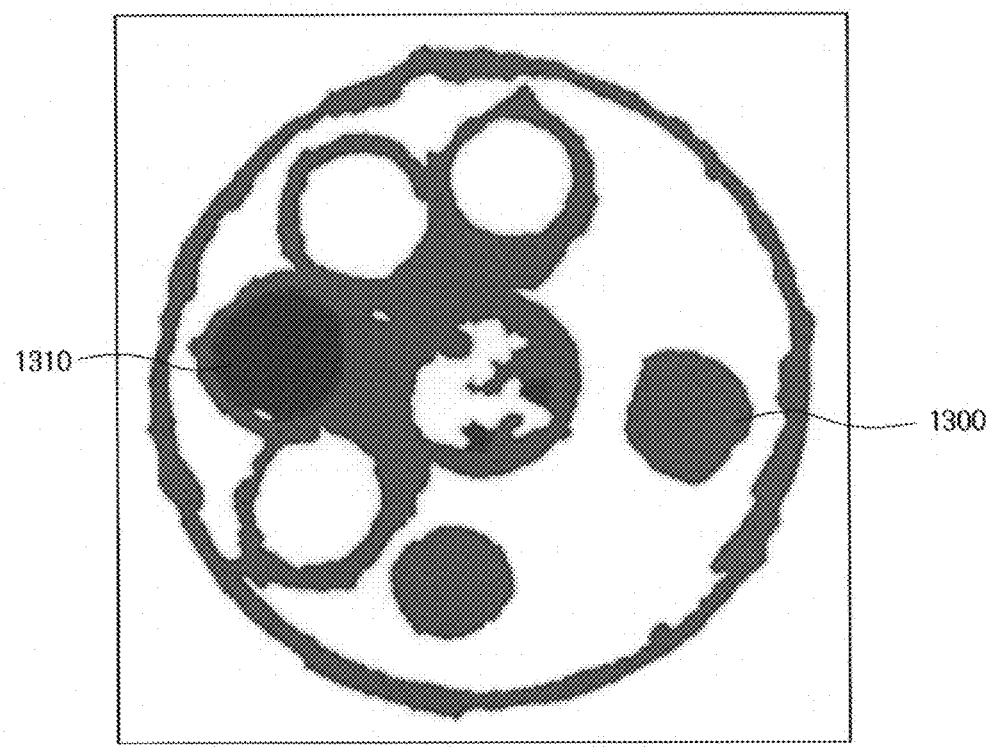
FIG. 13 illustrates classification of colors in pattern coloring of FIG. 10 into warm and cool colors.
Figure 14:
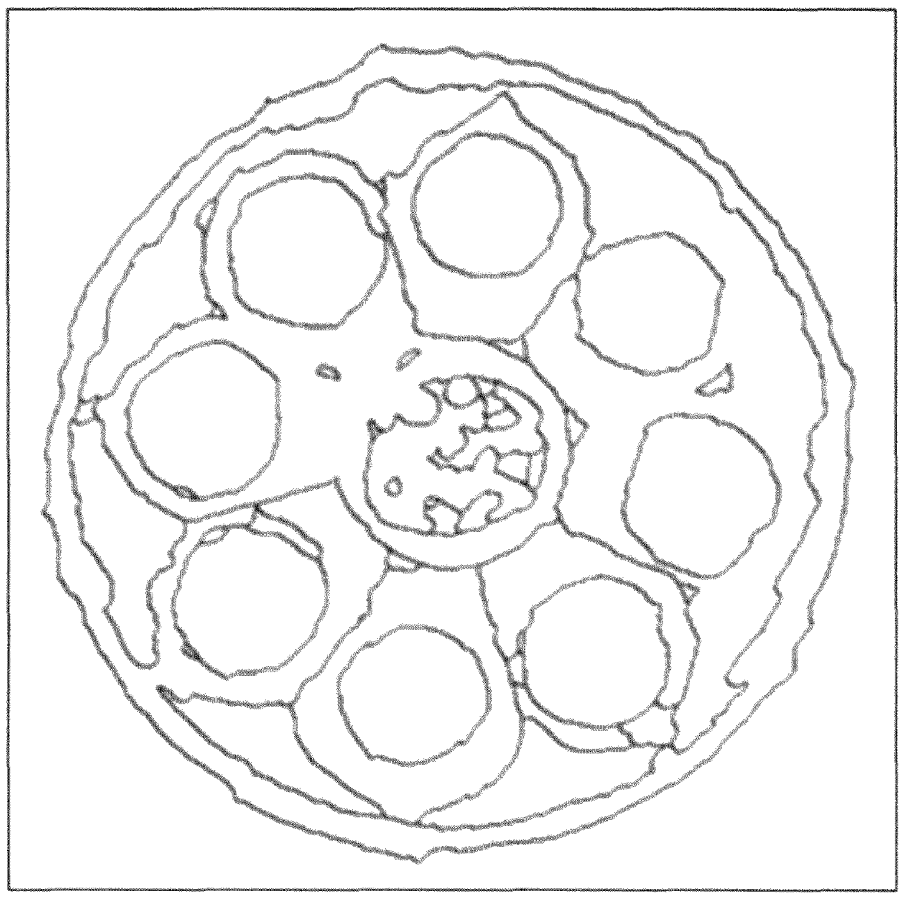
FIG. 14 illustrates the coloring clusters extracted by color-related elements analysis of pattern coloring of FIG. 10.
Figure 15:
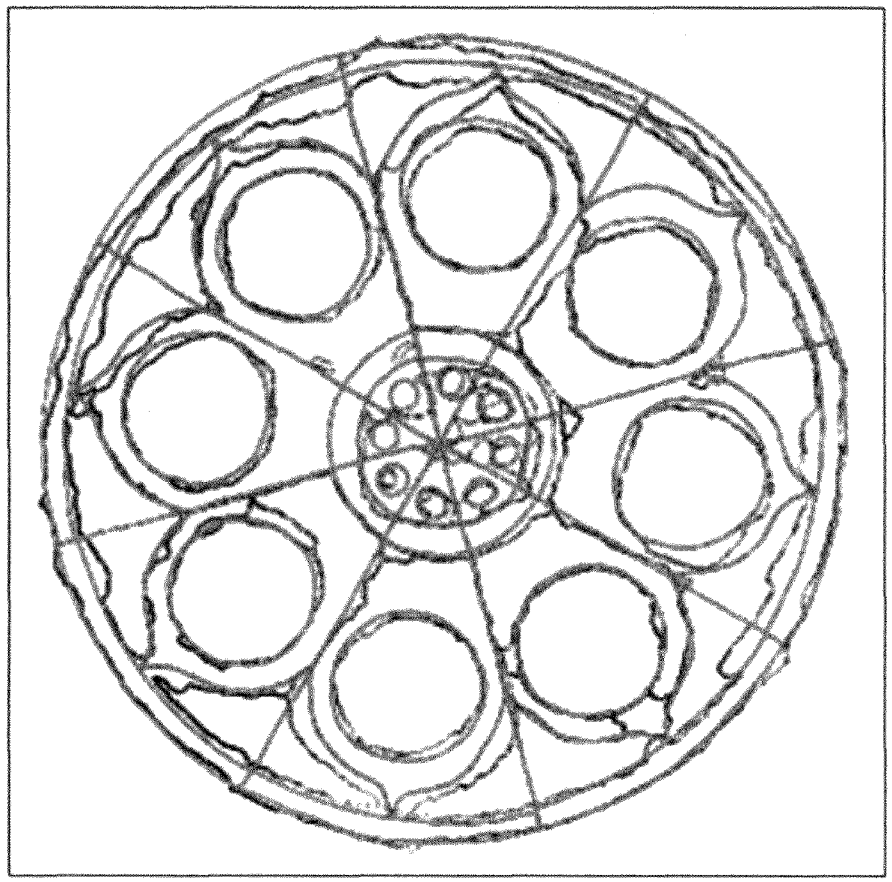
FIG. 15 illustrates overlap of coloring clusters with pattern clusters.
Figure 16:
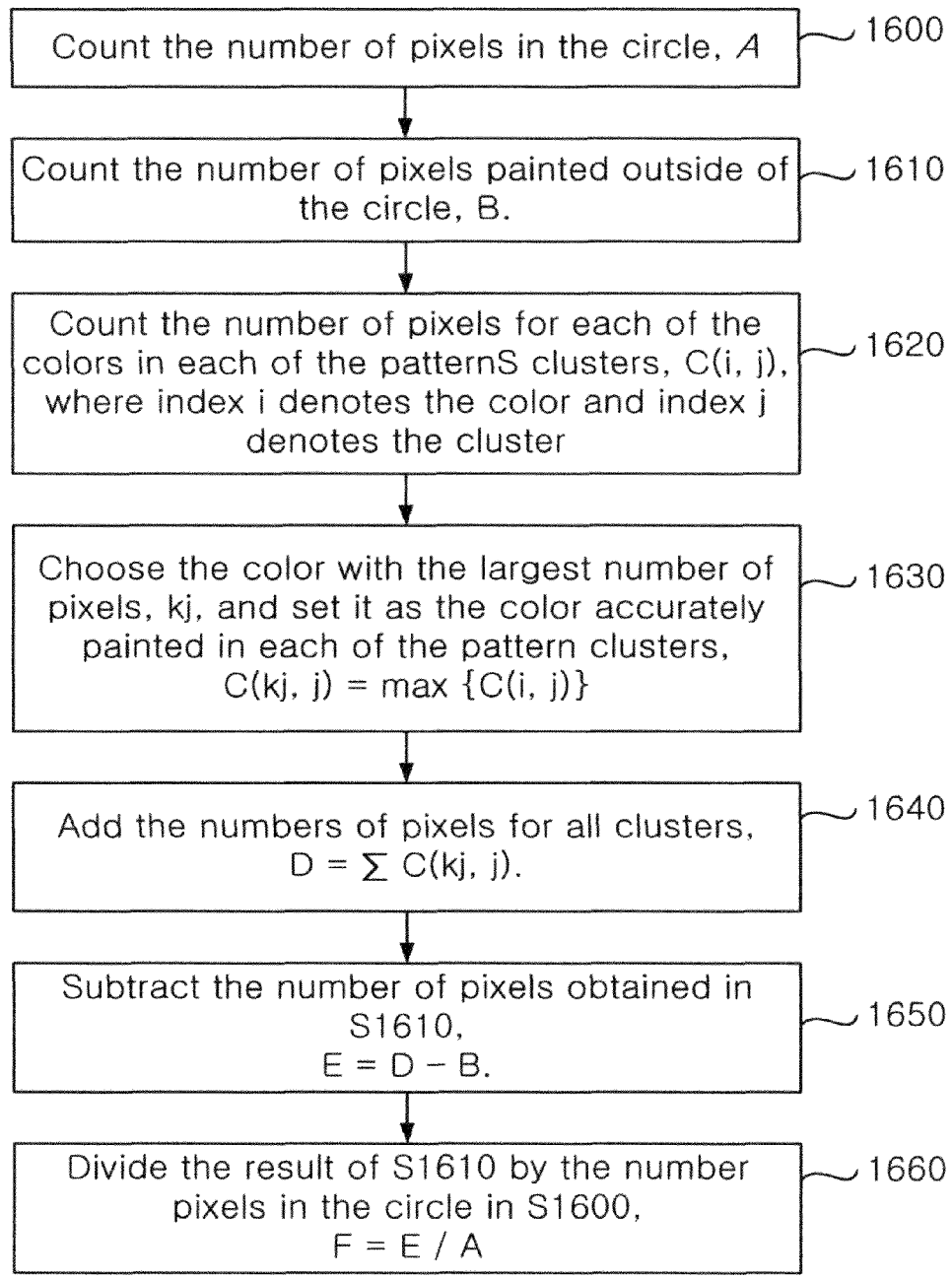
FIG. 16 is a flowchart of a method for measuring the accuracy according to a disclosed embodiment.
Figure 17:
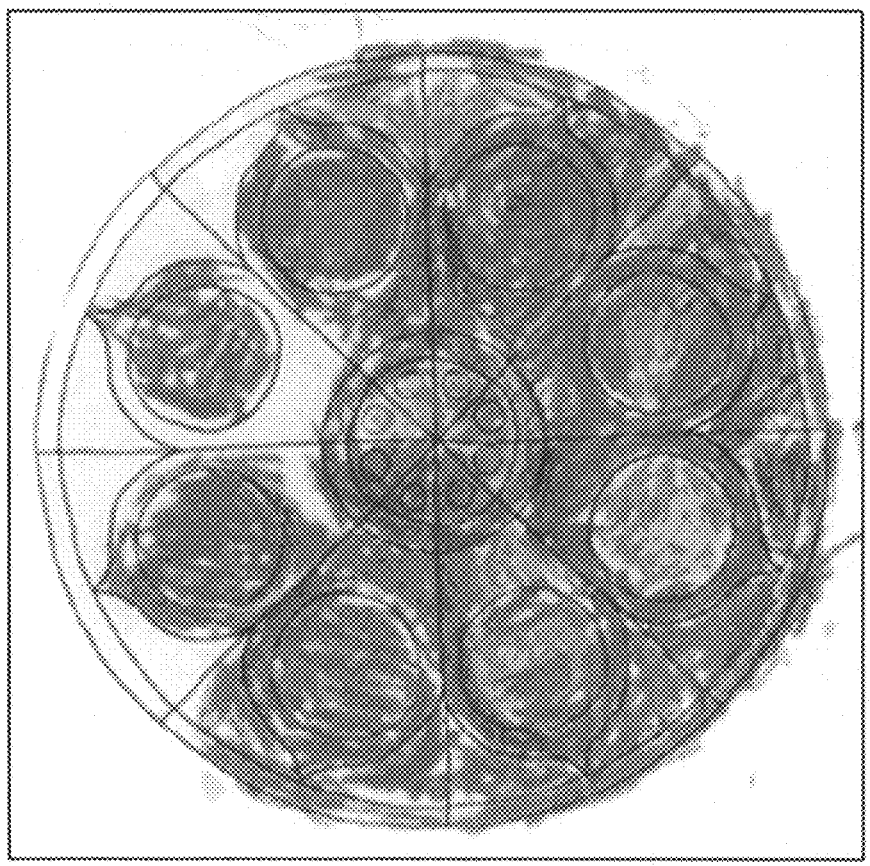
FIGS. 17 and 18 illustrate two samples of pattern colorings.
Figure 18:
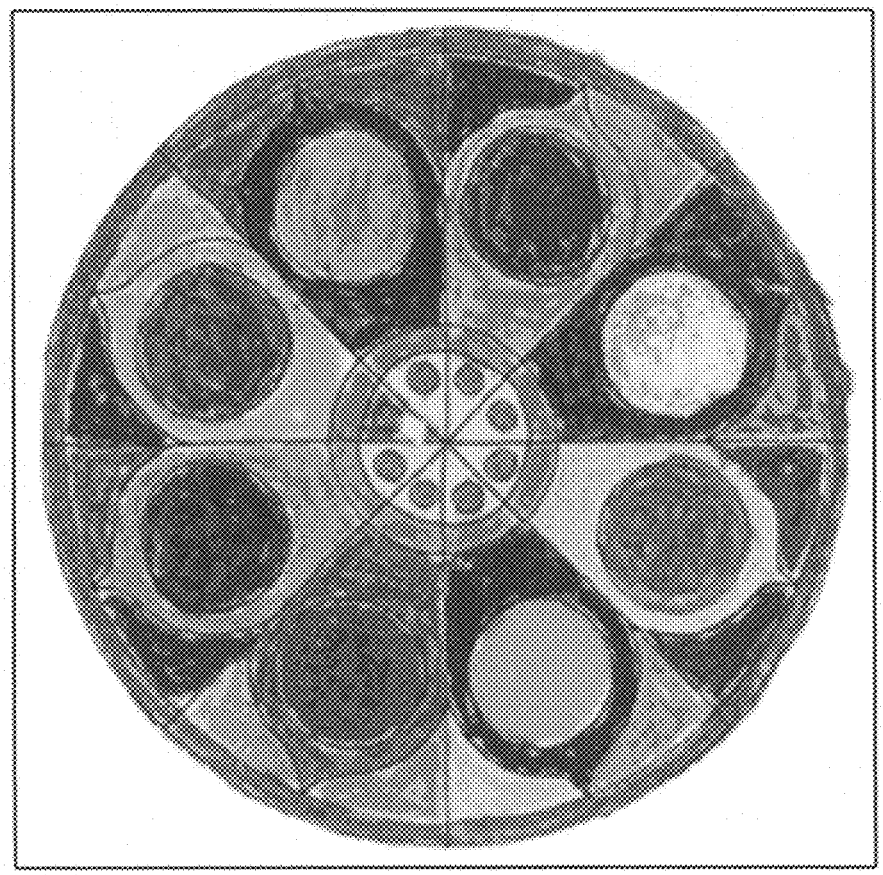

FIG. 4 is a block diagram of a pattern coloring analyzing unit according to a disclosed embodiment. FIG. 5 is a block diagram of color-related elements analyzing unit included in pattern colorings analyzing unit. FIG. 6 is a block diagram of performance-related elements analyzing unit included in the pattern colorings analyzing unit. FIG. 7 is a flowchart of the pattern colorings analyzing method according to a disclosed embodiment. FIG. 8 illustrates an example of patterns according to a disclosed embodiment. FIG. 9 is a pattern coloring of FIG. 8. FIG. 10 illustrates a case in which the colors in the pattern coloring are classified into one of the standard colors. FIG. 11 illustrates classification of colors in pattern coloring of FIG. 10 into main, subsidiary, and complementary colors. FIG. 12 illustrates classification of colors in pattern coloring of FIG. 10 into primary and secondary colors. FIG. 13 illustrates classification of colors in a pattern coloring of FIG. 10 into warm and cool colors. FIG. 14 illustrates coloring clusters extracted by color-related elements analysis of pattern coloring of FIG. 10. FIG. 15 illustrates overlap of coloring clusters with pattern clusters, and FIG. 16 is a flowchart of a method for measuring the accuracy according to a disclosed embodiment.

Referring to FIG. 4, the pattern colorings analyzing unit 11 includes an input unit 110, a noise eliminating unit 120, a color-related elements analyzing unit 130, and a performance-related elements analyzing unit 140. Referring to FIG. 5, the color-related elements analyzing unit 130 includes a color recognizing module 131, a color classifying module 133, a basic color-related element rating module 135, and an applied color-related rating module 137. Referring to FIG. 6, the performance-related elements analyzing unit 140 includes a completeness measuring module 141, an accuracy measuring module 143, and a degree of concentration determining module 145.

The input unit 110 receives a pattern colored by a client in step S200. A pattern colored by a client becomes a target of a pattern colorings analysis. Hereinafter, for the ease of understanding and convenience of description, it will be assumed that a suitable analysis target pattern includes the geometric mandala patterns and general picture patterns including, but not limited to, a person, bird, puppy, house, or tree.

A client colors the geometric mandala patterns, an example of which is the mandala pattern 800 of FIG. 8. An example of a picture (herein, referred to as an analysis target picture 900) which the client has colored is illustrated in FIG. 9.

The input unit 110 receives digital image files of pattern colorings scanned by a scanner or photographed by a digital camera. Suitable file formats include, but are not limited to, bitmap (BMP), the Graphics Interchange Format (GIF), Joint Photographic Experts Group (JPEG), Tagged Image Format (TIF), etc. The image files can be analyzed by the pattern colorings analyzing unit 11.

The noise eliminating unit 120 eliminates a noise in step S210. Here, the noise means unintended 'touch' or 'non-touch' of a coloring material, which occurs when the thickness of the tips of a coloring implement (for example, a pen, pencil, brush, crayon, or digital stylus) causes the drawer to color in unintended space or not fill in the intended space for coloring. The noise eliminating unit 120 eliminates the noises of a pattern coloring through a blurring process and a clustering process, but are well known in the art. The detailed descriptions of the blurring and clustering are omitted. In a case where the reliability of an analysis is intended to increase, the noise eliminating unit 120 may further be included in the pattern colorings analyzing unit 11.

The pattern colorings analyzing unit 11 analyzes the color-related elements and the performance-related elements of an input pattern coloring. The color-related elements and performance-related elements can be analyzed at the same time or in a specific order.

First, the color-related elements analyzing unit 130 analyzes the color-related elements in step S220. The color-related elements analyzing unit 130 recognizes the color in a pixel of a pattern coloring input to the input unit 110. A pattern coloring is divided into pixels to be analyzed. For example, a 480×640 pixel image would include 307,200 pixels.

Referring to FIG. 5, the color-related elements analyzing unit 130 includes a color recognizing module 131, a color classifying module 133, a basic-color related elements determining module 135, and an applied color-related elements determining module 137.

The color recognizing module 131 recognizes the color used in each pixel of a pattern coloring input to the input unit 110 in step S221.

The color classifying module 133 classifies a color recognized by the color recognizing module 131 into one of the predetermined standard colors in step S222. An appropriate color space for the coloring material is chosen. Appropriate color spaces include, but are not limited to, RGB, YUV, HSV, LUV, CIELAB and HVC.

Hereinafter, for the ease of understanding and convenience of description, some embodiments will be described on the basis of the 15 colors classification and/or the 47 colors classification. The 15 colors classification may use 15 standard colors defined by the Korean Standard Association 0011 (KSA 0011) in the HVC color space The color classifying module 133 classifies the color in each pixel into the color of nearest distance among the standard colors. The distance is a criterion measuring the color difference between two colors. For example, the distance between two colors $(h_1, v_1, c_1)$ and $(h_2, h_2, h_2)$ in the HVC space may be defined by the following Equation (1) suggested by the National Bureau of Standards (NBS).

$$dis[(h_1, v_1, c_1), (h_2, h_2, h_2)] = 1.2\left\{ 2c_1c_2\left[1 - \cos\left(\frac{2\pi(h_1 - h_2)}{100}\right)\right] + (c_1 - c_2)^2 + 16(v_1 - v_2)2 \right\}^{\frac{1}{2}} \quad (1)$$

According to another disclosed embodiment, there can be a bigger or smaller number of standard colors. For example, a color can be classified into one of 133 standard colors, and then into one of 47 standard colors, and then into one of 15 standard colors.

A pattern coloring file 1000, in which colors are classified into the 15 standard colors by the color classifying module 133, is illustrated in FIG. 10.

The basic color-related elements module 135 determines the basic color-related elements after the color classification by the color classifying module 133 in step S223.

The basic color-related elements may include, but are not limited to, the number and list of colors used, an area painted for each color, a number of clusters, an edge of colors, and a mixture of colors. The area painted denotes the number of pixels painted. A cluster refers to a continuous area painted with the same color, not separated by different colors. An edge may be denoted by pixels having a color different from that of the neighboring pixels.

The applied color-related elements determining module 137 determines an applied color-related elements from the basic color-related elements extracted in step S224 a knowledge base built beforehand. Applied color-related elements may include, but are not limited to, a main color, a subsidiary color, primary colors, secondary colors, warm colors, cool colors, and complementary colors.

The detailed description of examples of the applied color-related elements follows.

(i) Examples of a Main Color and a Subsidiary Color:

The main color is the color with the largest area, and the subsidiary color is a color with the second largest area. When the area of the main color is less than A % (e.g., 20% etc) of the whole area of the pattern (e.g., a circle included in the outermost portion of the mandala patterns), it may be assumed that no main color exists.

After color classifying the pattern coloring 900 of FIG. 9 into standard colors (see the reference numeral 100 of FIG. 10), the color covering the largest area is violet occupying 30.1% (see the reference numeral 1100 of FIG. 11), and the color covering the second largest area is red occupying 22.0%. Accordingly, these are determined as the main color and the subsidiary color, respectively.

(ii) Examples of a Primary Color and a Secondary Color:

The primary color includes red, blue and yellow, and the secondary color includes green, violet and orange. Here, the primary color is represented as yellow (see the reference numeral 1200 of FIG. 12), and the secondary color is represented as green (see the reference numeral 1210 of FIG. 12). According to the result of analysis, the primary color occupies 40.4%, and the secondary color occupies 34.0%.

(iii) Examples of a Complementary Color:

When the main color, the subsidiary color, and the color with the area larger than B % (e.g., 12% etc) of the whole pattern are (1) red and bluish green, (2) blue and orange, (3) indigo and orange, or (4) yellow and violet, or (5) green and purple, it is determined that complementary colors exist. Referring to FIG. 11, since yellow occupies 14.4% and is third most used color (see reference numeral 1110 of FIG. 11) and the title color is violet (see the reference numeral 1100 of FIG. 11), it is determined that the complementary colors of yellow and violet exist.

(iv) Examples of Warm Colors and Cool Colors:

The warm colors include red, orange and yellow, and the cool colors include blue and indigo. Referring to FIG. 13, the warm colors are represented to(as) red (see the reference numeral 1300 of FIG. 13), and the cool color are represented to(as) green (see the reference numeral 1310 of FIG. 13). According to the result of analysis, the warm colors occupy 40.4%, and the cool colors occupy 4.0%.

(v) Examples of Diversity of Color Tones:

The diversity of the color denotes the general concept of the use of a color, which is personally rated by the intuition, experience, or knowledge of an art therapist. An exemplary procedure of rating the diversity of the color includes the following two schemes. In the first scheme:

Step 1. The diversity of the color increases as the number of colors used increases.

Step 2. When the number of the colors used remains the same, the diversity of the color increases as the number of clusters increases. Here, a cluster refers to a contiguous area painted with the same color, not separated by different colors.

Step 3. When the number of the colors used and the number of the clusters are the same, the diversity of the color increases as the length of the outline increases.

In the second scheme:

The regression model of the statistical method is applied. In the regression model, a dependent variable is the rank of the diversity of color rated by art therapy experts. In the regression model, the independent variables include, but are not limited to, the number and the list of colors used, the number of clusters, and the length of edges. The independent variable of list of colors is expressed as indicator variables one less than the number of possible color tones.

As described above, the applied color-related elements determining module 137 can determine the various applied color-related elements from the basic color-related elements extracted by the basic color-related elements determining module 135.

In addition to the color-related elements analysis, the performance-related elements analyzing unit 140 analyzes performance-related elements in step S230.

Referring to FIG. 6, the performance-related elements analyzing unit 140 includes a completeness measuring module 141, an accuracy measuring module 143, and a degree of concentration determining module 145.

The completeness measuring module 141 measures the completeness of a pattern colored by a client through the target pattern 900 in step S231. The completeness is measured, for example, by the ratio of the number of pixels colored in the pattern to the number of pixels of the whole pattern (e.g., a circle disposed in the outermost portion of the base patterns of FIG. 8).

The accuracy measuring module 143 measures the accuracy of the coloring by the client through the analysis target picture 900 in step S232. The accuracy is the accordance of the coloring clusters with the pattern clusters. Here, a coloring cluster refers to a contiguous area painted with the same color and not separated by different colors, which can be obtained from the basic color-related determining module 135. A pattern cluster refers to an area surrounded by a closed line, without any other lines within it. Referring to FIG. 8, the number of the pattern clusters is 64. Referring to FIG. 14, the number of the coloring clusters in the illustrated example is 18. The overlap of a coloring cluster with a pattern cluster is illustrated in FIG. 15.

An algorithm for measuring the accuracy is illustrated in FIG. 16. FIG. 16 is a flowchart of an algorithm for measuring accuracy according to a disclosed embodiment. In the examples provided, the color of each pixel has been classified into one of the standard colors.

The accuracy measuring module 143 measures the accuracy quantitatively in a number through an algorithm with the following steps.

Step-1. Count the number of pixels in the circle, A, S1600.

Step-2. Count the number of pixels painted outside of the circle, B, S1610.

Step-3. Count the number of pixels for each of the colors in each of the pattern clusters, C(i, j), where index i denotes the color and index j denotes the cluster S1620.

Step-4. Choose the color with the largest number of pixels, $k_j$, and set it as the color accurately painted in each of the pattern clusters, C($k_j$,j).

Step-5. If white is chosen, assume that there exists no color accurately painted, S1640.

Step-6. Add the numbers of pixels for all clusters, D=ΣC($k_j$,j), S1650.

Step-7. Subtract the number of pixels obtained in Step-1, E=D−B, S1660.

Step-8. Divide the result of Step-7 by the number of pixels in the circle in Step-1, F=E/A, S1670.

Referring again to FIG. 7, the degree of concentration determining module 145 determines the degree of concentration based on the completeness measured by the completeness measuring module 141 in step S231 and accuracy measured by the accuracy measuring module 143 in step S232.

A degree of concentration may be related to the number of colors used and the number of clusters as well as the completion and the accuracy. Such a relationship will be described by the following exemplary regression model.

A number of m raters judge and rank the degree of concentration for each of the n samples of pattern colorings. The pattern coloring with the highest degree of concentration is Rank-1, the second highest Rank-2, and so on. The average of m ranks for sample i is denoted as $Y_i$, the dependent variable, which will be explained by the independent (explanatory) variables of the model. The number of colors, the number of color clusters, the completeness, and the accuracy are, respectively, the independent variables, which will explain the degree of concentration, $Y_i$.

By applying stepwise regression, some of the independent variables can be selected as important independent variables to explain the degree of concentration, the dependent variable. Moreover, to compare the relative effect (importance) of each independent variable on the dependent variable, a standardized regression model can be used:

The pattern colorings analyzing unit 11 can provide quantitative outputs or numbers corresponding to the color-related elements analyzed by the color-related elements analyzing unit 130 and the degree of concentration analyzed by the performance-related elements analyzing unit 140.

The pattern colorings analyzing unit 11 according to a disclosed embodiment provides quantitative, accurate and objective information such as the basic color-related elements (e.g., the number and list of colors used, the number of clusters, the length of edges, etc.), the applied color-related elements (e.g., the main color and the subsidiary color, the primary color and the secondary color, the complementary color, the warm color and the cool color, the diversity of color, etc.), the performance-related elements (e.g., completeness, accuracy, and the degree of concentration, etc.).

As described above, the psychological status or disorders evaluation unit 13 selects several elements (the basic color-related elements, the applied color-related elements, and the performance-related elements) analyzed by the pattern colorings analyzing unit 11, and evaluates psychological status or disorders using multiple linear regression models. More specifically, the psychological status or disorders evaluation unit 13 determines the degree of psychological status or disorders and whether it is serious or not.

Figure 19:
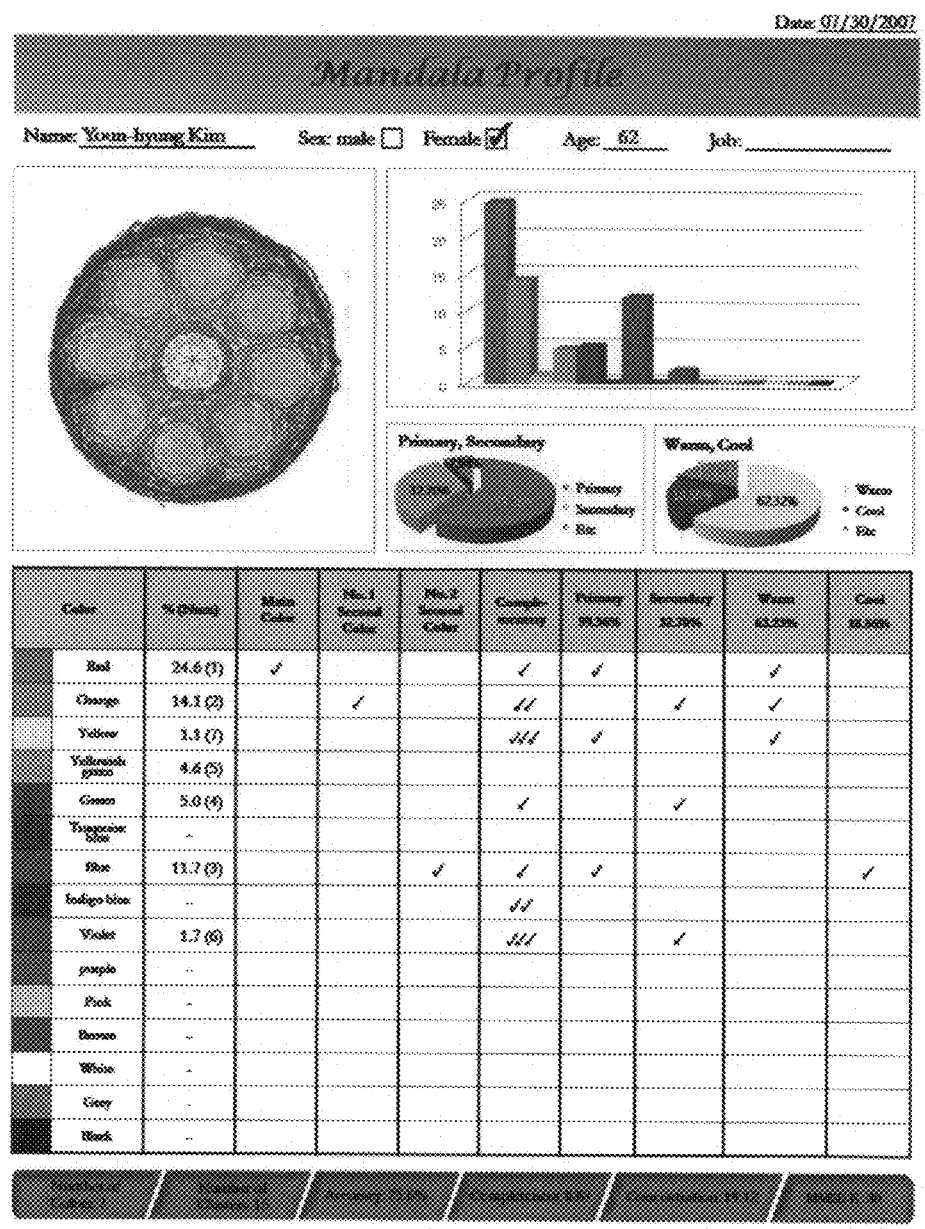
FIG. 19 illustrates analysis results of a pattern coloring according to a disclosed embodiment.

FIG. 19 illustrates analysis results of a pattern coloring by the pattern colorings analyzing unit 11 according to a disclosed embodiment. Referring to FIG. 19, basic color-related elements such as the number and list of colors used, the number of clusters, and the length of edges by the basic color determining module 135, applied color-related elements such as the main color and the subsidiary color, the complementary colors, the primary colors and the secondary colors and the warm colors and the cool colors by the applied color-related determining module 137, and the performance-related elements by the performance-related analyzing unit 140 such as the completeness by the completeness measuring module 141, the accuracy by the accuracy measuring module 143, and the degree of concentration by degree of concentration determining module 145 have been analyzed.

According to a disclosed embodiment, the level of psychological status or disorders (MMSE-K score) (Y) can be estimated by multiple linear regression models with stepwise method in which dependent variables are the elements analyzed by the pattern coloring analyzing unit 11. That is, the psychological status or disorders evaluation unit 13 estimates the level of psychological status or disorders.

According to another embodiment, it is possible to estimate the probability that the psychological status or disorders is serious. A regression model with stepwise method, where the dependent variable is set to Y=1 when the MMSE-K test score is below a certain value of C and set to Y=0 otherwise, where C is the threshold value used to determine the severity of the psychological status or disorders. That is, the psychological status or disorders evaluation unit 13 estimates the probability that the psychological status or disorders is serious.

In the following examples, one hundred mandala patterns painted by persons with suspected dementia were collected. An exemplary case of measuring the level of dementia, MMSE-K, is described.

Figure 20:
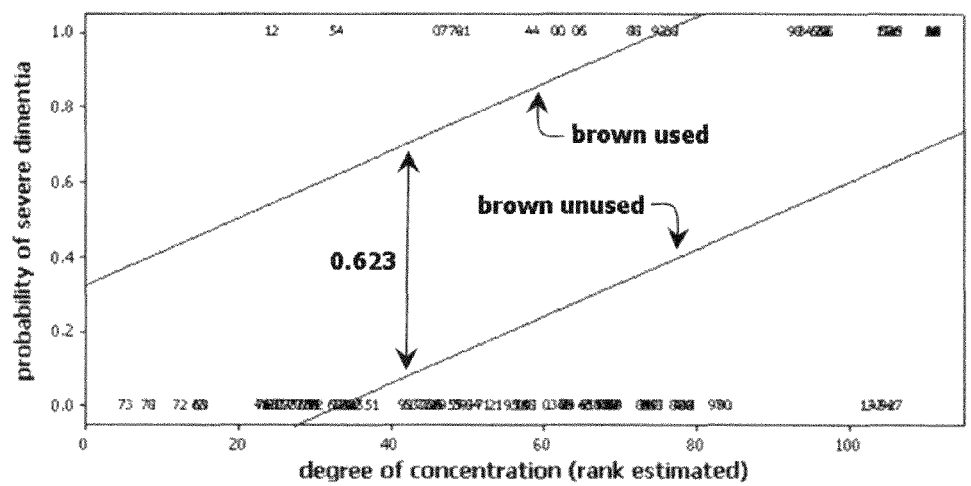
FIG. 20 is a graph illustrating the effects of the degree of concentration and color of brown on the probability of severe dementia.

The psychological status or disorders evaluation unit 13 evaluates the psychological status or disorders a client on the basis of results analyzed by the pattern colorings analyzing unit 11 (see FIG. 20), results obtained by the personal characteristics obtaining unit 12, and the knowledge base 14. The result is illustrated in FIG. 21.

Figure 21:
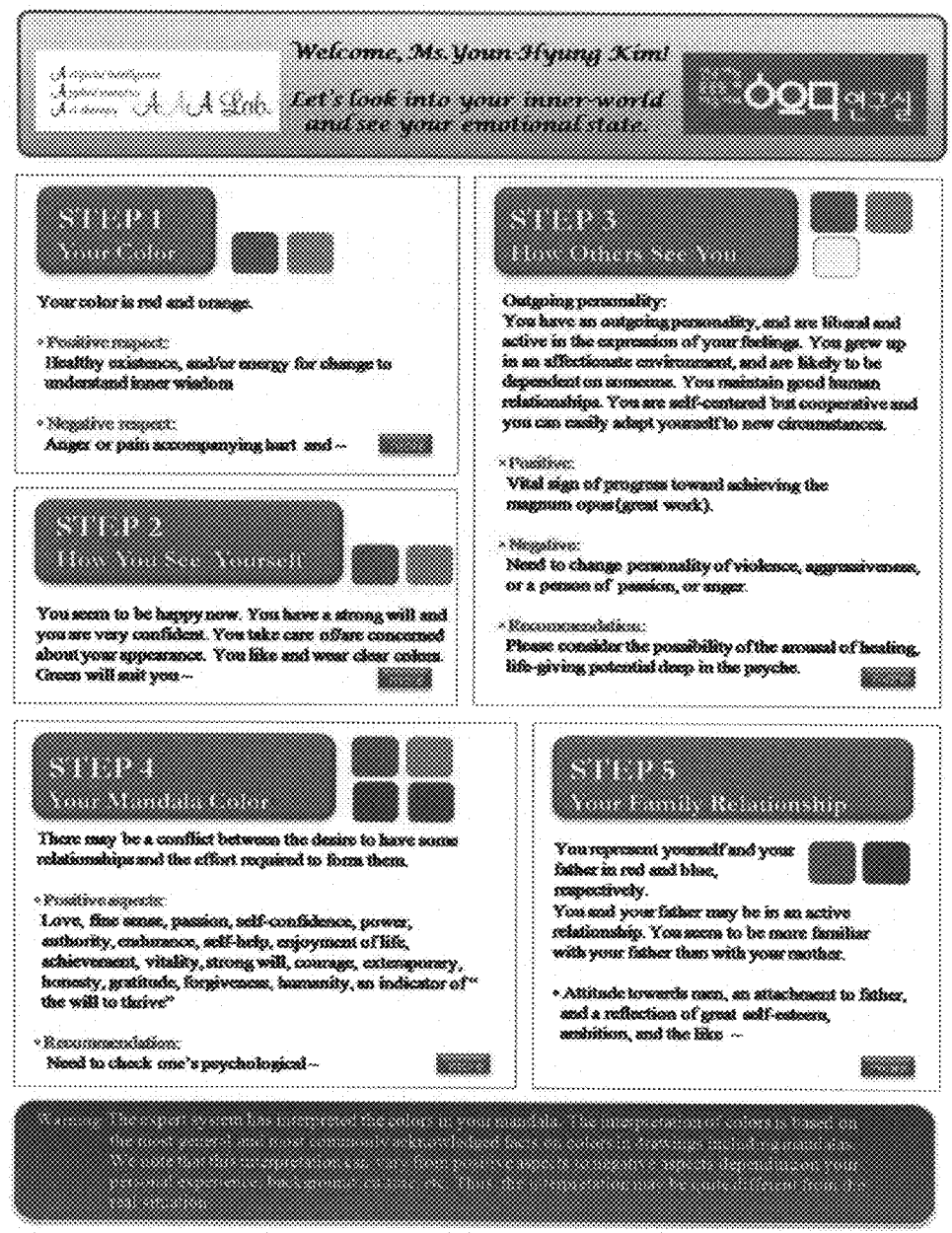
FIG. 21 illustrates evaluation of psychological status or disorders according to a disclosed embodiment.

The analysis results of FIG. 19 and/or FIG. 21 can be provided as a graph and a chart so that a user can easily understand them.

According to another embodiment, the psychological status or disorders evaluation apparatus 10 can detect the difference between two or more pattern colorings and thus can detect the change of psychological status or disorders of a client. At this point, the psychological status or disorders evaluation apparatus 10 may include the history database 15. The psychological status or disorders evaluating unit 13 compares the analysis results of the past picture stored in the history database 15 with the analysis results of a current picture analyzed by the pattern colorings analyzing unit 11, and detects and provides knowledge according to the results of the comparison. Therefore, the psychological status or disorders evaluating unit 13 detects the change of psychological status or disorders of the client.

Figure 22:
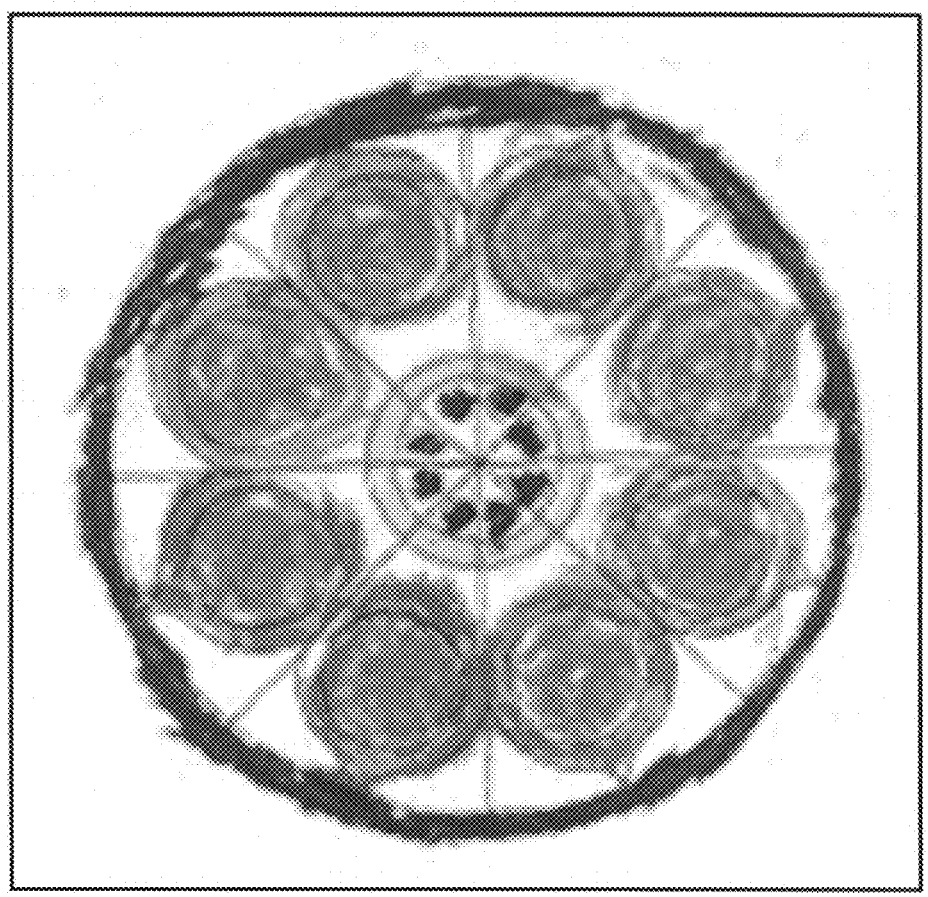
FIGS. 22 and 23 illustrate current and the past pattern colorings by a same client.
Figure 23:
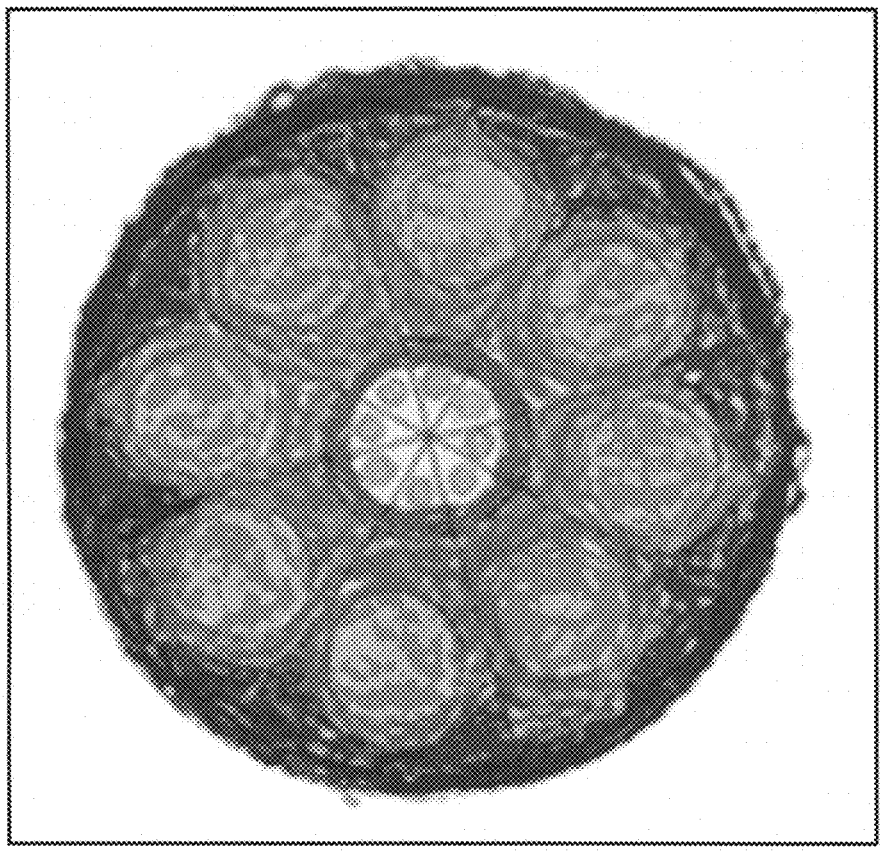

FIGS. 22 and 23 illustrate current and past patterns, respectively, colored by a same client. In the illustrated examples, the client responded on the questionnaire of FIG. 3.

Examining the differences in the two pattern colorings, the improvement of all the measures in the accuracy, number of colors used, number of clusters, completeness, and degree of concentration can be seen, and thus it is estimated that there have been positive changes in the psychological status. Also, there have been increasing percentages of primary colors and warm colors, and thus we estimate that there is a change of psychological or emotional status.

That is, the psychological status or disorders evaluation apparatus 10 provides the knowledge base 14 and detects the relevant knowledge in the knowledge base to the difference between two pattern colorings, and thus can detect the changes of psychological status or disorders of client.

The mandala pattern of FIG. 8 has been described as an exemplary analysis target pattern. However, the disclosed embodiments may be applied in conjunction with a variety of suitable analysis target patterns.

More specifically, the psychological status or disorders evaluation apparatus 10 according to a disclosed embodiment can provide a plurality of predetermined patterns to the client in a predetermined scheme. Furthermore, the client can select, arrange (or dispose) and color several certain patterns to make an analysis target pattern coloring.

For example, an analysis target pattern coloring may include at least one of a tree, a house and a person. In this case, a House-Tree-Person Drawing (HTP) analysis scheme may be applied.

For example, an analysis target pattern coloring may include the members of a family who are doing something. In this case, a Kinetic Family Drawing (KFD) analysis scheme may further be applied.

For example, an analysis target pattern coloring may include the patterns of a person picking an apple. In this case, a Person Picking an Apple from a Tree (PPAT) analysis scheme may further be applied.

The above-described examples have been described as embodiments, and it is apparent to one skilled in art therapy that it can be applied in parallel with plural known technologies.

In the selection and arrangement of patterns, a computer can automatically perform functions in the existing art therapy assessments tools including the existing House-Tree-Person Drawing (HTP), Kinetic Family Drawing (KFD), Person Picking an Apple from a Tree (PPAT), etc.

Disclosed herein, a method for analyzing pattern colorings can suggest new elements such as the completeness, the accuracy, and the degree of concentration during the coloring patterns, and provide objective and quantitative information in numbers by analyzing and rating the applied color-related elements and performance-related elements.

Disclosed herein, a method for analyzing pattern colorings can apply objective and quantitative information to art therapy through the analysis, rating, and evaluation of pattern colorings by automatically providing the objective and quantitative information in numbers.

Disclosed herein, a method for analyzing pattern colorings can apply scientific and quantitative information to art therapy through pattern colorings analysis by automatically providing the objective and quantitative information in numbers.

The method for the evaluation of psychological status or disorders can analyze elements and detect knowledge corresponding to the analysis results to provide the knowledge when any colored patterns are given by building the knowledge base related to the analysis of elements obtained through the analysis of pattern colorings and personal characteristics obtained by questionnaires.

The method for the evaluation of psychological status or disorders can detect the changes of colored patterns and provide corresponding knowledge when a series of colored patterns are given.

The method for the evaluation of psychological status or disorders can save art therapists the effort and time taken to analyze pattern colorings, by automatically analyzing many pattern colorings by computer in a short time.

The method for measuring accuracy, the method for analyzing pattern colorings, and the method for evaluating psychological status or disorders according to various embodiments can be realized as programs and stored in a computer-readable recording medium that can execute the programs. Examples of the computer-readable recording medium include, but are not limited to, CD-ROM, RAM, ROM, floppy disks, hard disks, magneto-optical disks and the like.

While multiple embodiments have been shown and described, various modifications to the described embodiments may be appreciated and made by those skilled in the art without departing substantially from the scope of the present disclosure, the following claims and their equivalents.

The invention claimed is:

1. A computer-implemented method for evaluating psychological status or disorders, comprising:
   obtaining personal characteristics of client from questionnaire;
   receiving a colored pattern from the client;
   rating color-related elements of pattern colorings in the received colored pattern;
   rating performance-related elements, said performance-related elements comprising completeness and accuracy of the pattern colorings;
   determining, using at least one computer processor, a degree of concentration of the pattern colorings;
   analyzing the pattern colorings by invoking predetermined knowledge from a knowledge base stored in memory relevant to the rated color-related elements, the rated performance-related elements, the determined degree of concentration, and the obtained personal characteristics; and
   detecting changes in evaluations or interpretations of psychological status or disorders based on differences between the analyzed pattern colorings and other analyzed pattern colorings of the client.

2. The computer-implemented method of claim 1, wherein the rating of the color-related elements comprises:
   eliminating noise of colors painted;
   recognizing a color used in each pixel of the pattern coloring;
   classifying the recognized color into one of predetermined standard colors;
   measuring the area painted with each of standard colors;
   detecting color edges;
   counting the number of clusters;
   measuring the length of edges;
   calculating the areas painted with primary and secondary colors;
   calculating the areas painted with cool and warm colors; and
   determining whether complementary colors exist.

3. The computer-implemented method of claim 1, wherein the rating of the completeness is performed by counting the number of pixels colored, the whole pixels of the pattern, and pixels colored outside of the pattern.

4. The computer-implemented method of claim 1, wherein the rating of the accuracy comprises: counting the number of pixels in a circle, A;
   counting the number of pixels painted outside of a circle, B;
   counting the number of pixels for each of the colors in each of pattern clusters, C(i, j), where index i denotes the color and index j denotes the cluster;
   choosing the color with the largest number of pixels, kj, and setting it as the color accurately painted in each of the pattern clusters, C(kj, j);
   if white is chosen, assuming that there exists no color accurately painted;
   adding the numbers of pixels for all clusters, D=.SIGMA.C (kj,j);
   subtracting the number of pixels painted outside of the circle from the result of the addition, E=D−B; and
   dividing the result of the subtraction by the number of pixels in the circle, F=E/A.

5. The computer-implemented method of claim 1, wherein the determining of the degree of concentration is performed by stepwise regression and standardized regression in which independent variables are the number and list of colors used, the number of clusters, the length of edges, the completeness, and the accuracy.

6. The computer-implemented method of claim 1, further comprising:
   determining a level of psychological status or disorders by a stepwise regression and a standardized regression in which independent variables are the number and list of colors, the number of clusters, the length of edges, the completeness, the accuracy, and the degree of concentration.

7. The computer-implemented method of claim 1, further comprising:
   determining a probability that a psychological status or disorder is serious by a stepwise regression and a standardized regression in which independent variables are the number and list of colors, the number of clusters, the length of edges, the completeness, the accuracy, and the degree of concentration, and in which dependent variable is an indicator variable.

8. The computer-implemented method of claim 1, wherein the detecting of the changes in evaluations or interpretations is performed by establishing a knowledge base and using the established knowledge base.

9. A computer apparatus for evaluating psychological status or disorders, comprising:
   an input unit for receiving pattern colorings and personal characteristics from a client;
   a pattern colorings analysis unit for analyzing, using computer processing components, color-related elements, a degree of completeness, accuracy, and a degree of concentration in the pattern colorings;
   a personal characteristics obtaining unit for providing a questionnaire to the client, and obtaining, using the computer processing components, the personal characteristics of the client based on replies to the questionnaire;
   a knowledge database stored in memory for storing relevant predetermined knowledge in art therapy and knowledge connecting the personal characteristics, the color-related elements, the degree of completeness, the accuracy, and the degree of concentration, to psychological status or disorders; and
   a psychological status or disorders evaluation unit for detecting, using the computer processing components, predetermined knowledge from the knowledge database related to at least of one of the personal characteristics, the color-related elements, the degree of completeness, the accuracy, and the degree of concentration, for an evaluation of psychological status or disorders of the client.

10. The computer apparatus of claim 9, wherein the apparatus further comprises a history database for storing the analysis results of the pattern colorings obtained by the pattern colorings analyzing unit, wherein the psychological status or disorders evaluation unit invokes the knowledge from the knowledge base on the basis of differences among analysis results of several pattern colorings stored in the history database, to evaluate the changes of psychological status or disorders in the client.

11. A computer-implemented method for evaluating a patient's psychological status, comprising:
   receiving personal characteristic parameters corresponding to a patient through a patient interface, the personal characteristic parameters including the patient's personal color preferences, color associations, and declared psychological state;
   receiving and analyzing colored pattern data using computer processing components, the colored pattern data including coloring data generated by the patient and pattern data defining a graphical outline to be colored by the patient;
   generating, using the computer processing components, a color rating corresponding to the analyzed colored pattern data including a color diversity parameter corresponding to at least one of a number of colors used, a list of colors used, an area painted with each color, a number of clusters, an edge and a mixture of colors;
   generating, using the computer processing components, a performance rating corresponding to the analyzed colored pattern data, the performance rating including a completeness parameter, an accuracy parameter and a concentration parameter corresponding to the completeness parameter and the accuracy parameter;
   performing stepwise multiple linear regression in which the independent variables include the color rating and the performance rating;
   applying logic from a knowledge base stored in memory, the knowledge storing predetermined data associating colored patterns, personal characteristics and psychological status; and
   generating, using the computer processing components, a current status analysis for the patient, the current status analysis indicating a degree and severity of the patient's psychological status.

12. The computer-implemented method of claim 11, wherein generating a color rating includes recognizing a color used in each pixel of the colored pattern data;
   classifying the recognized color based on the color difference between two colors according to a predetermined standard color space;
   determining basic color-related elements including at least one of a number and list of colors used, an area painted for each color, a number of clusters, and edge of colors, and a mixture of colors; and
   determining applied color-related elements based on the basic color-related elements, the applied color-related elements including at least one of a main color, a subsidiary color, primary colors, secondary colors, warm colors, cool colors and complementary colors.

13. The computer-implemented method of claim 11, wherein the concentration parameter is generated from stepwise multiple linear regression in which the independent variables are the number of colors, the number of color clusters, the completeness and accuracy.

14. The computer-implemented method of claim 11, further comprising: reducing noise from the colored pattern data to remove unintended coloring data.

15. The computer-implemented method of claim 11, further comprising: estimating a quantitative level of the patient's psychological status.

16. The computer-implemented method of claim 11, further comprising: estimating a probability that the patient's psychological status is serious.

17. The computer-implemented method of claim 11, further comprising: retrieving a previous status estimate corresponding to the patient from a historical database;
   comparing the previous status estimate to the current status estimate;
   detecting a change of the patient's psychological status based on the comparison between the previous status estimate to the current status estimate.

18. The computer-implemented method of claim 11, further comprising: modifying the logic stored in the knowledge base according to the patient's colored pattern data and current status estimate.

\* \* \* \* \*